United States Patent [19]
Mülleder et al.

[11] Patent Number: 5,773,655
[45] Date of Patent: Jun. 30, 1998

[54] PROCESS FOR THE PURIFICATION OF AN AQUEOUS SOLUTION OF A TERTIARY AMINE-OXIDE

[75] Inventors: Eduard Mülleder, Linz; Bruno Mangeng, Seewalchen; Franz Schwenninger, Königsdorf; Johann Männer, Weyregg, all of Austria

[73] Assignee: Lenzing Aktiengesellschaft, Lenzing, Austria

[21] Appl. No.: 817,818

[22] PCT Filed: Aug. 16, 1996

[86] PCT No.: PCT/AT96/00148

§ 371 Date: Apr. 15, 1997

§ 102(e) Date: Apr. 15, 1997

[87] PCT Pub. No.: WO97/07268

PCT Pub. Date: Feb. 27, 1997

[30]  Foreign Application Priority Data

Aug. 18, 1995  [AT]  Austria ..................... 1400/95

[51] Int. Cl.[6] ............ C07C 291/04; D01F 13/02
[52] U.S. Cl. ............ 564/298; 564/297; 210/638; 210/651; 210/663; 210/669; 210/670; 210/681; 210/683
[58] Field of Search ............ 564/297, 298; 210/638, 691, 663, 669, 670, 681, 683

[56]  References Cited

U.S. PATENT DOCUMENTS

| | | | |
|---|---|---|---|
| 5,053,138 | 10/1991 | Korger et al. | 210/670 |
| 5,094,690 | 3/1992 | Zikeli et al. | 106/198 |
| 5,178,764 | 1/1993 | Astegger et al. | 210/651 |
| 5,409,532 | 4/1995 | Astegger et al. | 106/163.1 |
| 5,441,689 | 8/1995 | Laity | 264/179 |
| 5,628,941 | 5/1997 | Kalt et al. | 264/38 |

FOREIGN PATENT DOCUMENTS

| | | |
|---|---|---|
| 356419 | 2/1990 | European Pat. Off. . |
| 427701 | 5/1991 | European Pat. Off. . |
| 468951 | 1/1992 | European Pat. Off. . |
| 488988 | 6/1992 | European Pat. Off. . |
| 553070 | 7/1993 | European Pat. Off. . |
| 254199 | 2/1988 | German Dem. Rep. . |
| 274435 | 12/1989 | German Dem. Rep. . |
| 9311287 | 6/1993 | WIPO . |

*Primary Examiner*—Richard L. Raymond
*Attorney, Agent, or Firm*—Baker & Botts, LLP

[57]  ABSTRACT

The invention is concerned with a process for the purification of an aqueous solution of a tertiary amine-oxide containing impurities partially present in a dissolved and partially in a non-dissolved, colloidal state, and is characterized by a combination of the steps of (A) removing from the aqueous solution substantially all of said impurities present in a non-dissolved, colloidal state and (B) contacting said aqueous solution obtained in step (A) with an ion exchanger.

14 Claims, No Drawings

PROCESS FOR THE PURIFICATION OF AN AQUEOUS SOLUTION OF A TERTIARY AMINE-OXIDE

This application is a 371 of PCT/AT96/00148, filed Aug. 16, 1996. The present invention is concerned with a process for the purification of an aqueous solution of a tertiary amine-oxide, which solution contains impurities partially present in a dissolved state and partially in a non-dissolved, colloidal state. In particular, the present invention is concerned with a process for the purification of precipitation baths of the amine-oxide process.

For some decades there has been searched for processes for the production of cellulose moulded bodies able to substitute the viscose process, today widely employed. As an alternative which is interesting among other reasons for its reduced environmental impact, it has been found to dissolve cellulose without derivatisation in an organic solvent and extrude from this solution moulded bodies, e.g. fibres, films and other moulded bodies. Fibres thus extruded have received by BISFA (The International Bureau for the Standardization of man made fibers) the generic name Lyocell. By an organic solvent, BISFA understands a mixture of an organic chemical and water.

It has turned out that as an organic solvent, a mixture of a tertiary amine-oxide and water is particularly appropriate for the production of cellulose moulded bodies. As the amine-oxide, primarily N-methylmorpholine-N-oxide (NMMO) is used. Other amine-oxides are described e.g. in EP-A - 0 553 070. A process for the production of mouldable cellulose solutions is known e.g. from EP-A - 0 356 419. For the purposes of the present specification and the present claims, the production of cellulose moulded bodies using tertiary amine-oxides generally is referred to as amine-oxide process.

In EP-A - 0 356 419, an amine-oxide process for the production of spinnable cellulose solutions is described, wherein as a starting material among other substances a suspension of cellulose in liquid, aqueous N-methylmorpholine-N-oxide (NMMO) is used. This process consists in transforming the suspension in a thin-film treatment apparatus in one single step and continuously into a mouldable solution. Finally, the mouldable solution is spun into filaments by a forming tool such as a spinneret and the filaments are passed through a precipitation bath.

The cellulose is precipitated from the solution in an aqueous spinning bath. The amine-oxide is accumulated in the spinning bath. The process liquids produced in this process may contain up to 30 weight % of amine-oxide. For the economy of the amine-oxide process it is of vital importance to recover the amine-oxide nearly completely and reuse it for the production of a mouldable cellulose solution.

In addition to the amine-oxide, colourless to intensively coloured degradation products of the amine-oxide process are also accumulated in the spinning bath. On the one hand, these may deteriorate the quality of the moulded bodies produced and on the other they may represent a safety risk, since under certain conditions the amine-oxide tends to show highly exothermic decomposition reactions. These substances have to be removed from the aqueous solution of the amine-oxide before it is concentrated.

The solutions of amine-oxide frequently contain inorganic cations and anions such as sodium, calcium and magnesium cations and chloride, sulfate etc. respectively, derived partly from the pulp employed in the process for the production of cellulose moulded bodies and partly from other substances used and formed in the process. When the solutions are evaporated and processed to concentrated aqueous solutions of the amine-oxide which may be reused in the process, these ions will be accumulated and will consequently cause deposits and incrustations in the evaporation plant.

Metal ions and metal particles which also may be derived from the pulp used or from metallic equipment parts employed in the process are also accumulated in the solution. It is known that in solutions of cellulose in aqueous amine-oxides, precisely theses metallic particles and ions may initiate frequently strong degradation reactions of the amine-oxide as well as of the cellulose.

Dye stuffs resulting from e.g. degradation products of compounds used in the amine-oxide process to stabilize the cellulose solutions, by accompanying substances of the pulp employed and particularly materials obtained by degradation reactions of the amine-oxide employed, also have negative effects on the amine-oxide process and particularly on the quality of the cellulose moulded bodies produced according to the process.

Further, the solutions contain organic anions produced for instance by degradation reactions of the tertiary amine-oxide and the cellulose.

The substances indicated are present in the solution partly in a dissolved and partly also in a colloidal state, as so-called turbidifying agents.

To assure the economy and safety of the amine-oxide process, it is necessary to remove all the described unwanted substances as completely as possible from the solution to be purified.

In the literature, a number of proposals for the purification of aqueous solutions of tertiary amine-oxides have already been made:

DD-A-254 199 describes a process for the purification of aqueous solutions of NMMO wherein the solution passes through an anion exchanger. In a first step, the anion exchanger contains an exchanger resin of a styrene/divinylbenzene copolymer charged with tertiary amino groups of the —$CH_2N(CH_3)_2$ type, and in a second step it contains quaternary ammonium groups of the —$CH_2N(CH_3)_3OH$ type as the functional group. It is described that the NMMO solution to be purified is dark at the beginning of the purification, brown to yellow after the first step and bright yellow to waterwhite after the second step.

By employing an anion exchanger, primarily the dye stuffs as well as organic and inorganic anions present in the solution are removed from the solution.

EP-A-0 427 701 describes a process for the purification of aqueous amine-oxide solutions wherein the purification is carried out in a single-step process using an anion exchanger comprising as the functional groups exclusively quaternary tetraalkylammonium groups of the formula —$CH_2$—$N^+(CH_3)_3X^-$ or —$CH_2$-$N^+[(CH_3)_2(CH_2OH)]X^-$, wherein $X^-$ denotes the anion of an inorganic or organic acid, whereafter the anion exchanger is regenerated by means of an aqueous acid solution. The anion $X^-$ is preferably derived from a volatile acid, particularly carbonic acid, formic acid or acetic acid. These acids are also proposed for regenerating the anion exchanger.

A drawback of the exclusive use of anion exchangers in purifying aqueous amine-oxide solutions consists in that the solutions thus treated have a high pH value which consequently implies a greater purification effort. Moreover, in these known processes alkaline and alkaline earth cations as well as partially basic degradation products (morpholine, N-methylmorpholine and other compounds) are not removed from the solution.

DD-A-274 435 describes a process for the regeneration of N-methylmorpholine-N-oxide by passing the aqueous NMMO solutions over exchanger columns filled with styrene/divinylbenzene copolymer containing $SO_3H$-groups until they reach their maximum equimolar load and by subsequently displacing the NMMO by equimolar amounts of sodium hydroxide.

However, the exclusive use of a cation exchanger is not convenient, since many unwanted substances cannot be removed from the solution by the cation exchanger.

Further methods for the treatment of amine-oxide containing waste waters of the amine-oxide process are described in EP-A-0 468 951.

In contrast to the proposals described so far based on the treatment of the solution to be purified with at least one ion exchanger or a system of functional groups capable of exchanging ions, in EP-A-0 488 988 a process for the purification of an aqueous NMMO solution, particularly a spinning bath solution, wherein the solution is contacted with absorbents and subsequently subjected to filtration, is introduced. According to this literature, aluminium oxide, silicium dioxide and/or carbon are preferably used as adsorbents. The NMMO absorbed at the adsorbent is washed out after the adsorption by means of water, while the unwanted substances which are to be removed remain at the adsorbent.

In International Patent Application WO 93/11287 it is proposed to carry out the regeneration of an anion exchanger employed for the purification of aqueous solutions of tertiary amine-oxides using an aqueous solution of a strong inorganic acid and afterwards caustic soda. Moreover it is proposed to pass the solution over a cation exchanger before or preferably after it has passed the anion exchanger. It is described that when using a strongly basic anion exchanger, the coloration of the exchanger resin caused by passing over the solution to be purified is so intense that a simple regeneration by caustic soda will not be sufficient to discolour the resin again. Thus, to maintain the capacity of the resin, it has to be treated additionally with a strong inorganic acid.

In WO 93/11287 it is further proposed to remove solids suspended in the solution from the solution before it passes through the ion exchanger. This may be carried out by means of filtration, and according to WO 93/11287 a coarse filtration is sufficient. Removal of the colloidal substances contained in the precipitation bath is not provided for in the process of WO 93/11287.

Tests carried out by the inventors of the present invention have shown that none of the purification processes wherein a ion exchanger is used is suitable for an industrial-scale regeneration of precipitation baths, since the endurance of the ion exchanger(s) is/are unsatisfactorily short. As the endurance, the period of time whereafter the ion exchanger has to be regenerated is meant.

It is the object of the present invention to provide a process for the purification of precipitation baths not having the above drawbacks and wherein the endurance of the ion exchanger(s) is/are prolonged.

The process according to the invention for the purification of an aqueous solution of a tertiary amine-oxide containing impurities partially present in a dissolved and partially in a non-dissolved, colloidal state, is characterized by a combination of the steps of (A) removing from the aqueous solution substantially all of the impurities present in a non-dissolved, colloidal state and (B) contacting the aqueous solution obtained in step (A) with an ion exchanger.

Surprisingly it has been shown that the removal of the impurities present in a non-dissolved, colloidal state, i.e. of the turbidifying agents, will prolong the endurance of the ion exchanger extraordinarily. Thus, in the process according to the invention it is not necessary to regenerate the ion exchangers as often as is required in the state of the art, i.e. without separating the colloidal impurities.

The impurities present in a non-dissolved, colloidal state may be removed from the aqueous solution by agglomerating them and filtering them out of the aqueous solution, a deep-bed filtration having shown the best results.

In this context it is mentioned that without agglomeration of the colloidal impurities it is not possible to separate these by means of filtration. E.g., when a deep-bed filtration is carried out, the particles not agglomerated would penetrate the filtration medium unhinderedly and thus obstruct ion exchangers provided subsequently.

Deep-bed filtration is particularly effective when the grain size of the filter medium employed in the deep-bed filtration becomes smaller with the flow direction. As a filter medium, gravel, pulp, sand, pumice stone, hydro anthracite or a combination thereof is best employed.

Agglomeration may be carried out by adding a flocculant to the aqueous solution.

Usually flocculants are used in exclusively aqueous separation systems, such as in waste water treatment in mineral extraction. It is surprising that flocculants are also effective in precipitation baths containing a tertiary amine-oxide.

Polymere flocculants used in the paper industry are often referred to as retention agents, depending on the size of their molecules. For the purposes of the present application, the term "flocculants" refers also to substances known as retention agents.

It has been shown that flocculants are excellently capable of agglomerating the colloidal substances of a spent precipitation bath of the amine-oxide process to particles which may be filtered out.

Flocculants containing an oligomer or a polymer substance have shown particularly good results.

The flocculant contains preferably a polyacrylamide.

Further it is preferred that the flocculant contains a condensate of dicyandiamide and formaldehyde or a polyaluminiumchloride.

The flocculant is best employed in a concentration of from 0,5 ppm to 10 ppm, based on the total amount of aqueous solution.

A preferred embodiment of the process according to the invention is characterized in that the aqueous solution obtained in step (A) is contacted with an adsorbing resin before step (B).

As an ion exchanger, an anion exchanger and a cation exchanger may be provided.

The process according to the invention is particularly appropriate for purifying a spent precipitation bath produced in the amine-oxide process containing up to 30 weight % of amine-oxide, N-methylmorpholine-N-oxide being preferably employed as the amine-oxide. Surprisingly it has been shown that even the presence of 30 weigth % of NMMO does not have any negative effect on the effectiveness of the process according to the invention.

Thus the invention is also concerned with a process for purifying a spent precipitation bath produced in the amine-oxide process comprising impurities in a dissolved and in a non-dissolved, colloidal state and containing up to 30 weight % of N-methylmorpholine-N-oxide, and is characterized by the following steps of (A) adding a flocculant to the precipitation bath, optionally after diluting it, to agglomerate the impurities present in a non-dissolved, colloidal state;

(B) separating the agglomerated impurities by means of deep-bed filtration, a substantially clear solution being obtained;

(C) contacting the clear solution obtained in step (B) with an adsorber resin to remove dyed substances, and thereafter (D) contacting the solution with an anion exchanger and a cation exchanger to further purify the solution.

By means of the following Examples, the invention will be described in more detail.

EXAMPLE 1

Measurement of turbidity

The turbidity of the solutions was measured by establishing a ratio between the intensity of the light beam entering the solution and the light beam leaving the solution. Any further absorption of light, e.g. by dyed substances, was levelled by measuring the diffused light caused by the turbidity. The values measured were levelled with a standardized reference solution and indicated in FTU (Formazine Turbidity Units)

The following measurements were carried out by means of the turbidity measurement apparatus TRF made by the company Drott, Germany:

The flocculant Praestol BC 853 (a cationic flocculant of cationized polyacrylamide, made by the company Stockhausen) was added up to a concentration of 10 ppm to a spent precipitation bath of the amine-oxide process containing approximately 20 weight % of NMMO and having a turbidity of 5 FTU. Afterwards the solution was filtered through a deep-bed filter having a bulk of pumice (grain size 3–5 mm) and arenaceous quarz (grain size approximately 1 mm). After the deep-bed filtration, the solution had a turbidity of only 0,4 FTU.

Subsequently, the filtered solution was passed over an adsorber resin (of the XUS 40285.00 type, made by the company Dowex) modified by tertiary amino groups. The eluate obtained was passed over a strongly basic anion exchanger (of the Lewatit MO 500 type, made by the company Bayer) having quaternary ammonium groups, as well as over a strongly acid cation exchanger (of the Lewatit SM type, made by the company Bayer) having sulphonic acid groups as functional groups.

The endurance of the anion exchanger until it had to be regenerated was approximately 70 hours, that of the cation exchanger approximately 240 hours.

For comparison, no flocculant was added to the precipitation bath, while the test was carried out identically to the above indicated. In this case, the turbidity of the solution after deep-bed filtration was 3 FTU.

The endurance of the anion exchanger dropped drastically already during the purification cyle to approximately 45 hours, that of the cation exchanger to about 170 hours.

EXAMPLE 2

Example 1 was repeated employing the flocculants Melflock 113 S (a condensation product of dicyandiamide and formaldehyde, made by the company Trostberg), Alzofix P9 (a condensation product of polyaluminiumchloride and dicyandiamide, made by the company Trostberg) and combinations of the Praestol BC 853 used in Example 1 with Melflock 113 S and with Alzofix P9. The results were similar to those indicated in Example 1.

We claim:

1. A process for the purification of an aqueous solution of a tertiary amine-oxide containing impurities partially present in a dissolved and partially in a non-dissolved, colloidal state, characterized by a combination of the steps of (A) removing from said aqueous solution substantially all of said impurities present in a non-dissolved, colloidal state and (B) contacting said aqueous solution obtained in step (A) with an ion exchanger.

2. A process according to claim 1, characterized in that said impurities present in a non-dissolved, colloidal state are removed from said aqueous solution by agglomerating them and filtering them out of said aqueous solution.

3. A process according to claim 2, characterized in that said agglomerated impurities are filtered out by means of deep-bed filtration.

4. A process according to claim 2, characterized in that said impurities present in a colloidal state are agglomerated by adding a flocculant to said aqueous solution.

5. A process according to claim 4, characterized in that a flocculant containing an oligomer or a polymer substance is added.

6. A process according to claim 5, characterized in that said flocculant contains a polyacrylamide.

7. A process according to claim 5, characterized in that said flocculant contains a condensate of dicyandiamide and formaldehyde.

8. A process according to claim 5, characterized in that said flocculant contains a polyaluminiumchloride.

9. A process according to claim 4, characterized in that said flocculant is used in a concentration of from 0,5 ppm to 10 ppb, based on the total amount of the aqueous solution.

10. A process according to claim 1, characterized in that the aqueous solution obtained in step (A) is contacted with an adsorber resin before step (B).

11. A process according to claim 1, characterized in that as an ion exchanger an anion exchanger and a cation exchanger is provided.

12. A process according to claim 1, characterized in that as said aqueous solution of a tertiary amine-oxide a spent precipitation bath produced in the amine-oxide process containing up to 30 weight % of amine-oxide is used.

13. A process according to claim 1, characterized in that said tertiary amine-oxide is N-methylmorpholine-N-oxide.

14. A process for the purification of a spent precipitation bath produced in the amine-oxide process comprising impurities in a dissolved and in a non-dissolved, colloidal state and containing up to 30 weight % of N-methylmorpholine-N-oxide, characterized by the following steps of (A) adding a flocculant to said precipitation bath, optionally after diluting it, to agglomerate said impurities present in a non-dissolved, colloidal state;

(B) separating said agglomerated impurities by means of deep-bed filtration, a substantially clear solution being obtained;

(C) contacting said clear solution obtained in step (B) with an adsorber resin to remove dyed substances, and thereafter (D) contacting said solution with an anion exchanger and a cation exchanger to further purify said solution.

* * * * *